April 20, 1971 E. G. ALDRIDGE ET AL Plant Pat. 3,047

HYDRANGEA PLANT

Filed Aug. 21, 1969

INVENTORS,
EDGAR G. ALDRIDGE
LOREN L. ALDRIDGE
BY Rummler & Snow
Attys

United States Patent Office

Plant Pat. 3,047
Patented Apr. 20, 1971

3,047
HYDRANGEA PLANT

Edgar G. Aldridge, Bessemer, and Loren L. Aldridge, Birmingham, Ala., assignors to Aldridge, Inc., Birmingham, Ala.

Filed Aug. 21, 1969, Ser. No. 852,124
Int. Cl. A01h 5/00
U.S. Cl. Plt.—54 1 Claim

ABSTRACT OF THE DISCLOSURE

A new variety of hydrangea plant characterized by its very large and showy flower clusters which include an unusually large number of flowers, all flowers being sterile and each consisting of numerous petaloid-sepals. The mature sepals are white and slowly turn to green and ultimately to brown. The plant branches extensively, grows to a height of about six feet, blooms continuously and profusely from April to August and the foliage turns to a deep wine color in autumn.

BACKGROUND OF THE INVENTION

Our new variety of hydrangea plant was discovered by us, as a seedling, in our gardens at Bessemer, Ala. The origin of the plant is unknown. We noted, however, its distinction over other varieties of hydrangea plant in our gardens, particularly in its growth habit and the very large and showy flower clusters which appeared profusely over the entire plant and bloomed continuously from spring to fall. Further investigation showed that all of the flowers were sterile, a factor appearing to be the reason for its unusually showy blooms, and we then decided to propagate this discovery for commercial purposes.

Propagation of this new variety was first done by cuttings at our gardens at Bessemer, Ala., and continued asexual propagation, by cuttings, has demonstrated that the unusual and distinctive characteristics of this plant are fixed and hold true from generation to generation.

DESCRIPTION OF THE DRAWINGS

Our new variety of hydrangea plant is illustrated in the accompanying photographic drawings in which the upper view shows the entire plant in full bloom; and the lower view shows two of the panicles or flowering stems as cut flowers and in somewhat more detail.

DESCRIPTION OF THE NEW PLANT

Figure 1:
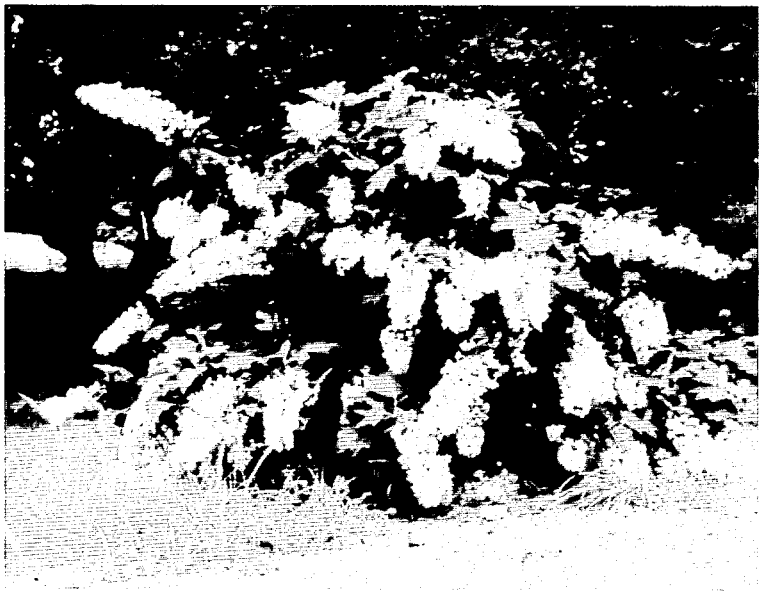
Figure 2:
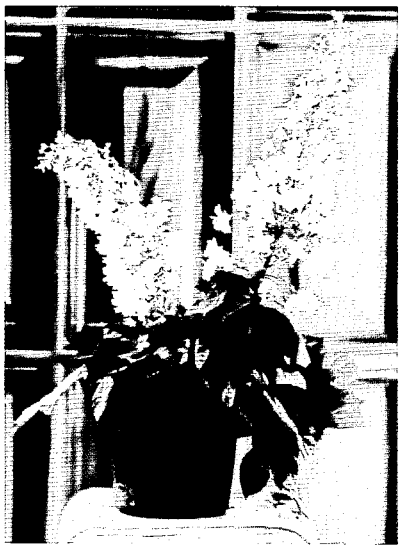

The following is a detailed description of our new variety of hydrangea plant with color designations according to "A Dictionary of Color" by Maerz and Paul.

*THE PLANT*

Origin: Seedling.
Parentage: Unknown.
Classification: *Hydrangea quercifolia* Bartram var.
Form: Shrub.
Height: Up to about 2 meters.
Growth: Sturdy, upright and vigorous.
Branching: Extensive.
Foliage:
*Quantity.*—Abundant.
*Shape of leaf.*—Lobed and finely serrated.
*Size of leaf.*—20 cm. long by 15 cm. wide.
*Texture.*—Slightly leathery.
*Color.*—Upper side—green (Plate 24, Column H, Row 9); under side—grayish green (Plate 24, Column C–E, Row 6–7); Foliage turns to a deep wine color in autumn.
*Ribs and veins.*—Prominent.
*Petioles.*—7 to 10 cm. long.

*The bud*

Form: Hemispherical and consisting of white, imbricated sepals.
Size: 1 to 3 mm. in diameter.
Aspect: Smooth.
Rate of opening: Very slow—sepals separate.
Peduncle: Sturdy and strong. 30 to 45 cm. long.

*The flower*

Blooming habit: Continuous and profusely from the first of May to the first of August.
Size: Diameter up to 40 mm.
Borne: By panicle having long, strong peduncle.
Shape: Flat. Form changes as blooms mature. Sepals elongate and stem lengthens.
Sepals-petaloids: Up to 40 in number.
Size: Up to 15 mm. wide by 20 mm. long.
Color: Mature sepals are white and slowly change to green. (Pl. 19, Col. C–D–E, Row 4) Green sepals change to rose (Pl. 6, Col. A through K, Row 3) and then rose sepals become brown (Pl. 15, Col. E, Rows 7 through 10) as the bloom ages. Green sepals may become brown without passing through the rose stage.
Texture: Soft—membranaceous.
Appearance: Showy.
Persistence: Hangs on and dries—may remain until following spring.
Disease resistance: Not subject to any known disease.
Fragrance: None.
Lasting quality:
*On plant.*—Excellent.
*As a cut flower.*—Good.
Reproductive organs: None.
Fruit: None.

Our new variety of hydrangea plant most resembles the typical *Hydrangea quercifolia* Bartram (unpatented) and also resembles *Hydrangea arborescens* grandiflora, which is sold commercially as "Hills of Snow" (unpatented).

The typical *Hydrangea quercifolia* Bartram produces both fertile and sterile flowers. The fertile flowers are not showy whereas the sterile flowers are showy, ray flowers located at the margins of the panicle but consisting of only four or five petaloid-sepals. Our new variety produces no fertile flowers, has longer, stronger panicles and many more flowers on each panicle. Also, each flower is extraordinarily large and consists of numerous petaloid-sepals, many more than the flowers of other varieties, with the result that each full blooming panicle appears heavy and full with a large solid mass of flower petals from end to end.

We claim:

1. A new and distinct variety of hydrangea plant substantially as shown and described herein, characterized by its continuous blooming habit and profuse production of very large and strong panicles each bearing large, showy flowers, each of which consists of up to forty relatively large petaloid-sepals.

No references cited.

ROBERT B. BAGWILL, Primary Examiner